United States Patent
De Benedetto et al.

(10) Patent No.: US 12,109,024 B2
(45) Date of Patent: Oct. 8, 2024

(54) PULSE OXIMETRY DEVICE, SYSTEM AND METHOD

(71) Applicant: LIFE METER SRL, Chieti (IT)

(72) Inventors: Fernando De Benedetto, Chieti (IT); Alberto Visconti, Chieti (IT); Marco Raimondi, Chieti (IT); Matteo Aventaggiato, Chieti (IT)

(73) Assignee: LIFE METER SRL, Chieti (IT)

( * ) Notice: Subject to any disclaimer, the term of this patent is extended or adjusted under 35 U.S.C. 154(b) by 993 days.

(21) Appl. No.: 17/045,272

(22) PCT Filed: Apr. 5, 2019

(86) PCT No.: PCT/EP2019/058734
§ 371 (c)(1),
(2) Date: Oct. 5, 2020

(87) PCT Pub. No.: WO2019/193196
PCT Pub. Date: Oct. 10, 2019

(65) Prior Publication Data
US 2021/0169382 A1    Jun. 10, 2021

(30) Foreign Application Priority Data
Apr. 5, 2018   (GB) .................................. 1805703

(51) Int. Cl.
*A61B 5/00*    (2006.01)
*A61B 5/0205*    (2006.01)
(Continued)

(52) U.S. Cl.
CPC .......... *A61B 5/1495* (2013.01); *A61B 5/0205* (2013.01); *A61B 5/14552* (2013.01);
(Continued)

(58) Field of Classification Search
CPC . A61B 5/1495; A61B 5/0205; A61B 5/14552; A61B 5/6802; A61B 5/6833;
(Continued)

(56) References Cited

U.S. PATENT DOCUMENTS

| | | | |
|---|---|---|---|
| 4,621,643 A * | 11/1986 | New, Jr. ............... | A61B 5/1495 |
| | | | 250/252.1 |
| 4,913,150 A | 4/1990 | Cheung et al. | |

(Continued)

FOREIGN PATENT DOCUMENTS

| | | |
|---|---|---|
| EP | 3289967 | 3/2018 |
| WO | 2011013132 | 2/2011 |

(Continued)

OTHER PUBLICATIONS

Search Report for UK Application No. GB1805703.4, mailed Apr. 1, 2019.
(Continued)

*Primary Examiner* — May A Abouelela
(74) *Attorney, Agent, or Firm* — Andrus Intellectual Property Law, LLP

(57) ABSTRACT

A method of measuring blood oxygenation consists of measuring Sp02 on one or more test subjects using a first, reference pulse oximetry device (100), such as a medical-grade pulse-oximeter of the kind that employs, for example, a finger-tip clip-type probe. This can be done on each patient over relatively short time periods. Then, the Sp02 is monitored on a target subject across a relatively longer time period using a second, wearable pulse oximetry device (10) that can be worn non-intrusively by the target use, for example in the form of a bracelet. The Sp02 measured using the wearable pulse oximetry device (10), can be measured based on calibration measurements performed using the first, reference pulse oximetry device (100). In this way, the measurements produced by the wearable pulse oximetry device (10) are calibrated using a medical-grade pulse-oximeter (100).

9 Claims, 6 Drawing Sheets

(51) Int. Cl.
   *A61B 5/1455*   (2006.01)
   *A61B 5/1495*   (2006.01)
   *G16H 10/60*    (2018.01)
   *G16H 40/40*    (2018.01)
   *G16H 40/67*    (2018.01)
   *G16H 50/30*    (2018.01)
   *G16H 50/70*    (2018.01)
   *A61B 5/024*    (2006.01)

(52) U.S. Cl.
   CPC .......... *A61B 5/6802* (2013.01); *A61B 5/6833* (2013.01); *G16H 10/60* (2018.01); *G16H 40/40* (2018.01); *G16H 40/67* (2018.01); *G16H 50/30* (2018.01); *G16H 50/70* (2018.01); *A61B 5/02433* (2013.01); *A61B 2560/0214* (2013.01); *A61B 2560/0238* (2013.01); *A61B 2560/0456* (2013.01)

(58) Field of Classification Search
   CPC ........ A61B 5/02433; A61B 2560/0214; A61B 2560/0238; A61B 2560/0456; A61B 5/6824; A61B 5/14551; A61B 5/681; G16H 10/60; G16H 40/40; G16H 40/67; G16H 50/30; G16H 50/70
   See application file for complete search history.

(56) References Cited

U.S. PATENT DOCUMENTS

| | | | | |
|---|---|---|---|---|
| 6,770,028 B1* | 8/2004 | Ali | ................ | A61B 5/742 600/300 |
| 10,238,305 B2* | 3/2019 | Hingorani | .......... | A61B 5/02438 |
| 11,183,303 B2* | 11/2021 | Matichuk | ............... | A61B 5/681 |
| 2002/0125991 A1* | 9/2002 | Levin | ................ | A61B 5/14551 340/286.07 |
| 2003/0236452 A1* | 12/2003 | Melker | .............. | A61B 5/14551 600/323 |
| 2004/0024297 A1 | 2/2004 | Chen et al. | | |
| 2005/0075548 A1* | 4/2005 | Al-Ali | ................ | A61B 5/0002 600/300 |
| 2006/0135860 A1 | 6/2006 | Baker et al. | | |
| 2006/0149144 A1* | 7/2006 | Lynn | ..................... | A61B 5/145 600/323 |
| 2006/0189871 A1* | 8/2006 | Al-Ali | ................. | A61B 5/7475 600/476 |
| 2007/0038050 A1* | 2/2007 | Sarussi | ............... | A61B 5/6826 600/324 |
| 2007/0073116 A1* | 3/2007 | Kiani | ................. | A61B 5/14552 600/310 |
| 2007/0100221 A1* | 5/2007 | Sato | ................... | A61B 5/14552 600/323 |
| 2007/0191697 A1* | 8/2007 | Lynn | ................. | A61B 5/08 600/323 |
| 2007/0244377 A1* | 10/2007 | Cozad | ................. | A61B 5/6829 600/323 |
| 2008/0103375 A1* | 5/2008 | Kiani | ................ | A61B 5/0002 600/323 |
| 2009/0043180 A1* | 2/2009 | Tschautscher | ....... | A61B 5/6838 600/323 |
| 2009/0247850 A1* | 10/2009 | Porges | ............... | A61B 5/14551 600/323 |
| 2010/0049023 A1* | 2/2010 | Sterling | ............... | A61B 5/6816 600/363 |
| 2010/0324386 A1* | 12/2010 | Moon | ................ | A61B 5/02125 600/324 |
| 2010/0324389 A1* | 12/2010 | Moon | ................ | A61B 5/0245 600/324 |
| 2012/0016219 A1* | 1/2012 | Fujii | .................... | A61B 5/6826 600/324 |
| 2012/0130203 A1* | 5/2012 | Stergiou | ................ | G16H 50/20 600/301 |
| 2012/0179011 A1* | 7/2012 | Moon | ................ | A61B 5/6826 600/324 |
| 2012/0190947 A1 | 7/2012 | Chon et al. | | |
| 2013/0131475 A1* | 5/2013 | Eisen | .................... | A61B 5/7207 600/324 |
| 2013/0172691 A1* | 7/2013 | Tran | ....................... | A61B 8/565 600/595 |
| 2013/0218039 A1* | 8/2013 | Sotos | .................... | A61B 5/681 600/529 |
| 2013/0338459 A1* | 12/2013 | Lynn | .................... | A61B 5/0205 600/323 |
| 2014/0200423 A1* | 7/2014 | Eisen | .................... | A61B 5/742 600/340 |
| 2014/0213863 A1 | 7/2014 | Loseu et al. | | |
| 2014/0235980 A1* | 8/2014 | Whitfield | ............. | A61B 5/0205 600/528 |
| 2014/0288435 A1 | 9/2014 | Richards et al. | | |
| 2014/0296670 A1* | 10/2014 | Vastola | ............... | A61B 5/14552 600/324 |
| 2015/0099941 A1* | 4/2015 | Tran | ...................... | A61B 5/1112 600/300 |
| 2015/0131098 A1 | 5/2015 | Yang et al. | | |
| 2015/0196251 A1* | 7/2015 | Outwater | ........... | A61B 5/14551 600/324 |
| 2016/0073954 A1* | 3/2016 | Meitav | ............... | A61B 5/02055 600/479 |
| 2016/0081628 A1* | 3/2016 | Melkoniemi | ............ | A61B 5/01 600/301 |
| 2016/0100780 A1* | 4/2016 | Vastola | ............. | A61B 5/68335 600/340 |
| 2016/0287166 A1* | 10/2016 | Tran | ....................... | A61B 5/74 |
| 2016/0345881 A1 | 12/2016 | Sarantos et al. | | |
| 2016/0360971 A1* | 12/2016 | Gross | .................... | A61B 5/4833 |
| 2016/0361004 A1* | 12/2016 | Lange | ................... | A61B 5/6826 |
| 2017/0027459 A1 | 2/2017 | Shimuta | | |
| 2017/0049336 A1* | 2/2017 | Hatch | .................. | A61B 5/6833 |
| 2017/0065188 A1* | 3/2017 | Jain | ....................... | A61B 5/0215 |
| 2017/0325744 A1 | 5/2017 | Allec et al. | | |
| 2017/0156615 A1* | 6/2017 | Shirazi | ............... | A61B 5/14551 |
| 2017/0173262 A1* | 6/2017 | Veltz | ....................... | G16H 20/17 |
| 2017/0251962 A1* | 9/2017 | Shiho | .................... | A61B 5/742 |
| 2017/0303834 A1* | 10/2017 | Bechtel | ................ | A61B 5/1075 |
| 2017/0303861 A1* | 10/2017 | Bechtel | ................ | A61B 5/14552 |
| 2017/0319114 A1 | 11/2017 | Kaestle | | |
| 2017/0367599 A1 | 12/2017 | Sanyal | | |
| 2018/0001980 A1* | 1/2018 | Hulbert | ............. | G08B 21/0453 |
| 2018/0014781 A1 | 1/2018 | Clavelle et al. | | |
| 2018/0020960 A1* | 1/2018 | Sarussi | ............... | G01N 33/4925 600/310 |
| 2018/0035943 A1 | 2/2018 | Shemesh et al. | | |
| 2018/0092581 A1* | 4/2018 | Heanue | ............. | A61B 5/14551 |
| 2018/0110450 A1* | 4/2018 | Lamego | ............. | A61B 5/0022 |
| 2018/0132794 A1* | 5/2018 | Lange | ................... | G16H 40/63 |
| 2018/0154097 A1* | 6/2018 | Matsumoto | ........... | A61M 16/06 |
| 2018/0192965 A1* | 7/2018 | Rose | ..................... | A61B 5/0002 |
| 2018/0279892 A1* | 10/2018 | Qi | ........................ | A61B 5/7214 |
| 2018/0333088 A1* | 11/2018 | Holz | .................... | A61B 5/1032 |
| 2019/0008396 A1* | 1/2019 | Baron | ................. | A61B 5/14552 |
| 2019/0090813 A1* | 3/2019 | Nover | ................... | A61B 5/6831 |
| 2019/0090886 A1* | 3/2019 | Brown | ............... | A61B 17/1322 |
| 2019/0117159 A1* | 4/2019 | Peeters | .............. | A61B 5/02438 |
| 2019/0167124 A1* | 6/2019 | Verkruijsse | ........ | A61B 5/14552 |
| 2019/0246967 A1* | 8/2019 | Pekander | ............. | A61B 5/14552 |
| 2019/0282169 A1* | 9/2019 | Chen | .................... | A61B 5/6886 |
| 2020/0015723 A1* | 1/2020 | Eisen | ................... | A61B 5/14552 |

FOREIGN PATENT DOCUMENTS

| | | |
|---|---|---|
| WO | 2013030744 | 3/2013 |
| WO | 2014026200 | 2/2014 |
| WO | 2016053942 | 4/2016 |

(56) References Cited

FOREIGN PATENT DOCUMENTS

| WO | 2016110781 | 7/2016 |
|----|------------|--------|
| WO | 2016193735 | 12/2016 |

OTHER PUBLICATIONS

Rusch, et al. "Signal Processing Methods for Pulse Oximetry", Computers and Biology in Medicine, vol. 26, No. 2, published Mar. 1, 1996.
Forstner, "Pulsoximetrie: Stand und Entwicklung der Technik", Biomedizinische Technik, Fachverlag Schiele un Schoen GmbH, vol. 33, No. 3, published Sep. 10, 1988.
International Search Report and Written Opinion for PCT/EP2019/058734, mailed Jul. 9, 2020.
Examination Report for UK Application No. GB1805703.4, mailed Aug. 12, 2020.
Combined Search and Examination report for UK Application No. 1805703.4, mailed Oct. 8, 2018.

\* cited by examiner

PULSE OXIMETRY DEVICE, SYSTEM AND METHOD

CROSS-REFERENCE TO RELATED APPLICATIONS

This application is the U.S. national stage application of International Application PCT/EP2019/058734, filed Apr. 5, 2019, which international application was published on Oct. 10, 2019, as International Publication WO 2019/193196 in the English language. The international application is incorporated herein by reference, in entirety. The international application claims priority to GB Patent Application No. 1805703.4, filed Apr. 5, 2018, which is incorporated herein by reference, in entirety.

TECHNICAL FIELD

The present invention relates to a device for measuring and/or monitoring blood oxygenation. In particular, the present invention relates to a "medical-grade" device for measuring and/or monitoring blood oxygenation. With "medical-grade" we mean that the present invention relates to a device for measuring and/or monitoring blood oxygenation that enables medical diagnosis in a subsequent phase, or as a subsequent step, ie after pulse oximetry data have been collected. The present invention thus also relates to a medical pulse-oximeter for collecting heart rate and SpO2 data. The present invention also relates to a system comprising said device, such as a system for elaborating and/or communicating and/or presenting said data, and to related methods, such as calibration methods and/or device installation methods on one or more patients and/or methods of presenting and/or communicating said data and/or methods of operating said system.

BACKGROUND

Medical doctors carry out diagnoses based on biometric data acquired on the human body. Pulse oximetry is a biometric technique that simultaneously measures heart rate and blood oxygenation by estimating oxygen saturation levels in haemoglobin in peripheral arterial blood.

Certain pulse oximetry methods are based on non-invasive detection of light reflected, scattered or otherwise transmitted through a peripheral tissue perfused with blood. These methods are generally collectively referred to as photoplethysmography. Accordingly, a photoplethysmographic signal (or, PPG signal) is collected by at least one PPG sensor, and then analysed. A subclass of these methods relies on the estimation of a blood oxygenation parameter known in literature as "peripheral capillary oxygen saturation" or "SpO2". SpO2 is calculated as the fraction of oxygenated haemoglobin over the total haemoglobin transported by the (peripheral, capillary) blood. The theory shows that this parameter can be linked to certain characteristics of the detected light, as will be described further herein.

The above pulse oximetry methods are preferred over invasive methods which, instead, require access to the blood. Invasive methods measure directly oxygen levels in one or more blood samples, and the corresponding measured parameter is known as "arterial blood oxygen saturation" or "SaO2". Since oxygen is only removed from blood in capillaries, SpO2 can provide an estimate of SaO2. Conveniently, this indirect measurement of SaO2 can be obtained by measuring certain properties of light which has interacted with a peripheral tissue irrorated with blood. Pulse oximetry is recognised as having the potential to provide highly accurate blood oxygenation estimates.

The present application focusses exclusively on devices, systems and methods for estimating SpO2.

Although SpO2 is calculated from measured characteristics of a detected light, and is therefore in more appropriate terms only estimated, or calculated, to align with terminology more often used in practice in the present application we refer to the estimation or calculation of the SpO2 parameter as the "measurement" of SpO2. However, it will be clear that what the systems described herein actually measure are one or more properties of detected light and then estimate or calculate SpO2 based on these measured properties of the detected light.

SpO2 "measurements" must accurately represent the level of blood oxygenation to be medically relevant, and thus potentially form the basis for medical diagnosis.

A set of SpO2 measurements must also be internally consistent to be medically applicable, so that patterns and trends in the data can be recognised and diagnosis performed.

It is also important to be able to acquire SpO2 measurements on a patient at regular intervals, or at least very frequently throughout a complete periodic time window, for example of the duration of 24 hours, so that the data may encompass different patient conditions related to the patient's everyday life such as sleeping, working, walking and exercising, amongst others.

The above requirements, however, pose various technical challenges.

The measurements may not be accurate or may lack consistency. This may be due to intrinsic measurement artefacts introduced, for example, by the respiratory activity of the patient, or by external patient conditions such as, for example, physical exercise.

Patient motion of any kind may in principle displace the sensors or alter their contact with the skin of the subject.

There is also the problem that the measurements may be adversely affected by other patient variables, such as skin elasticity and/or pigmentation, which vary with different patients.

There are also other variables which may adversely affect the repeatability of the measurements (for example, temperature), and many of these are discussed in the literature.

The prior art has attempted to mitigate the above problems.

It is known to perform heart rate measurements using a first pulse-oximeter on the human body, and simultaneously perform SpO2 measurements using a second pulse-oximeter at a nearby location on the same human body using different devices that employ different techniques. Similar artefacts are thus likely to affect the measurements collected from each device. These artefacts can thus be recognised and accordingly their adverse effect on any measurements averaged out, smoothened and/or reduced to improve the accuracy or consistency of the SpO2 measurements.

Patients may be confined to a monitoring space, such as a hospital room, so that the SpO2 measurements can be taken by medical-grade recording apparatus available on site. Such apparatus is certified for medical use and is thus relied upon to provide sufficient accuracy and sufficient consistency for medical diagnosis, at least in these controlled conditions. However, this equipment is only typically available for use in said monitoring spaces, where the patients are under controlled monitoring conditions. Further, the presence of clips and wires connecting the sensors with a central measurement unit makes it difficult to use such apparatus off site.

The above shortcomings could in principle be mitigated by implementing wireless communication. However, the sensors would still need to be provided as part of clip probes, such as finger clip probes or ear clip probes, so that the measurements would still be carried out on portions of the human body such as a finger's tip or an ear's lobe known to be sufficiently perfused with arterial blood. This may in principle lead to medically acceptable measurements.

Clips of any type, however, are not ideal, since they limit the range of activities that the patient can carry out outside the hospital room. For example, a patient wearing a clip probe on a finger, or on an ear lobe, is likely not to behave naturally in his/her workplace or at home, to reduce or eliminate physical exercise, or not to be able to sleep properly. These events may be detrimental to medical diagnosis based on collected SpO2 measurements.

On a different note, non-medical wearable pulse oximeters have been proposed in recent times and it is expected that in due course these devices will become generally increasingly available to the public as lifestyle aids. Some of these wearable devices will include bracelets wearable around the wrist. As such, these devices will be discreet and non-invasive. Whilst the corresponding pulse oximetry readings (italicised text is used here to affirm a contrast between blood oxygenation 'readings' in lifestyle devices and blood oxygenation 'measurements' in medical-grade devices via the estimation of the SpO2 parameter; see further the paragraph below) will be generally informative of the user's level of blood oxygenation, and will therefore be used by the device to suggest certain lifestyle actions to the user, or by the user to decide, for example, to change a lifestyle behaviour (for example do more physical exercise, or go to see a doctor), they will very unlikely be medically or clinically acceptable, since a medical doctor would not consider these readings to be appropriate for medical diagnosis, at least in connection with certain conditions which may be difficult to diagnose without accurate, repeatable, consistent, reliable and/or frequently collected data over sufficiently extended periods of time such as a whole 24-hour cycle.

The term reading has been used in the paragraph above to denote SpO2 measurements carried out by non-medical devices in a non-medical contexts and/or for non-medical purposes. This is in contrast with the meaning given herein to terms such as estimate or measurement of SpO2, which instead denote medically relevant SpO2 data gathered using a novel pulse oximetry device and/or related systems and methods.

It is the aim of at least one aspect or at least one embodiment of the presently disclosed pulse oximetry devices, systems and/or methods to mitigate at least one of the above shortcomings associated with the prior art.

SUMMARY OF THE INVENTION

According to an aspect of the present disclosure, there is provided a pulse oximetry device for measuring blood oxygenation, the device comprising:
one or more light emitters adapted to emit light directed into a human tissue;
at least one light detector for detecting the light emitted from said one or more light emitters after the light has passed through, ie has transited, said human tissue;
wherein the device is adapted to convert one or more measured characteristics of the detected light into corresponding SpO2 measurements,
wherein said conversion is based upon calibration data obtained from a plurality of reference SpO2 values measured using a different, reference pulse-oximeter.

The pulse oximetry device is thus advantageously calibrated against the reference pulse-oximeter.

The pulse oximetry device may be adapted to measure light intensity. In other words, the one or more characteristics measured by the pulse oximetry device may comprise a light intensity. As an alternative, the pulse oximetry device may be adapted to measure light absorption.

The pulse oximetry device may advantageously comprise two light emitters for emitting two respective substantially monochromatic lights at different wavelengths. A particularly advantageous configuration is when the pulse oximetry device comprises a red light and an infrared light. However, the red light may be substituted by a green light. Otherwise, the green light may be provided in addition to the red and infrared lights, for example by providing a third light emitter.

The pulse oximetry device may advantageously be adapted to calculate a parameter R derivable as a function of continuous and alternate components of the one or more detected lights. For example, when two light emitters are provided, one emitting a red light and one emitting an infrared light, R is calculated as follows:

$$R = \frac{RedAC/RedDC}{InfraRedAC/InfraRedDC},$$

wherein RedAC is an AC component of the light having the red wavelength, RedDC is a DC component of the light having the red wavelength, InfraRedAC is an AC component of the light having the infrared wavelength and InfraRedDC is a DC component of the light having the infrared wavelength. AC and DC components of a green light, respectively GreenAC and GreenDC, may replace RedAC and RedDC, respectively, in the equation shown above, when a green light is provided in substitution of the red light. Other formulations of the parameter R are however believed to be possible, at least in principle, depending on the configuration of the light emitters and/or detectors.

Accordingly, the pulse oximetry device may be adapted to measure SpO2 as a function of the parameter R described above. However, other useable parameters appear to have been proposed in literature and may be useable instead of R.

The light detector may be adapted to detect light reflected or scattered back towards the device. However, other acquisition modes would in principle be possible, for example using transmitted light.

Advantageously, the reference pulse-oximeter may be a medical-grade pulse-oximeter, such as a medically certified pulse-oximeter. This will contribute to the accuracy of the measurements.

The medical-grade, reference pulse-oximeter may comprise a clip probe.

The reference pulse-oximeter may comprise one or more wires for transmitting signals from the clip probe to a measurement unit of the reference pulse-oximeter. Clip probes are known, and examples are a finger clip or an ear clip probes.

The one or more reference SpO2 values may have been measured using the reference pulse-oximeter on two or more test subjects. The plurality of test subjects may advantageously be a large plurality of test subjects. This is advantageous since it would deliver a more robust calibration. Accordingly, the pulse oximetry device may then be used on different target subjects without further calibrations. However, further calibration data may subsequently become available once more test subjects have been tested to acquire calibration data.

The pulse oximetry device may comprise a memory and the calibration data may be stored locally on said memory.

The calibration data may define a linear relationship between the SpO2 measurements and the parameter R. However, at least in principle, other relationships would appear to be possible, depending on the characteristics of the sensors used and/or the parameters measured. If the pulse oximetry device and the reference pulse-oximeter measure different physical parameters, then obtaining the calibration data may comprise taking into account and/or compensating for, the relationship existing between said different parameters.

Some devices may be adapted to perform at least one post-calibration correction of the SpO2 measurements. This correction may be specific to a target subject being subjected to the SpO2 measurements. The correction may be based on at least one correction value, which may be applicable across all the SpO2 measurements. For example, said at least one correction value may comprise an offset. Said offset may be calculated as a difference between an SpO2 measurement performed by the device and a corresponding, reference SpO2 value taken by the reference pulse-oximeter.

The pulse oximetry device may be in the form of a pulse oximetry bracelet for measuring blood oxygenation on a wrist of a user.

The bracelet-type device may accommodate the one or more light emitters and the at least one light detector. Further, this device may also include said memory.

The pulse oximetry device may further comprise a processor programmed to perform said measurement of the one or more characteristics of the detected light and to perform said conversion.

Certain pulse oximetry devices may further comprise visual and/or display means for producing an output related to the SpO2 measurements. The display means may be adapted to monitor the SpO2 measurements over a predetermined time period, for example a day or a week.

According to another aspect of the present disclosure, there is provided a system comprising, in combination, a device as described herein and a docking station for docking the device thereto, wherein the device and the docking station may be operable to exchange data therebetween.

The docking station may further be adapted to wirelessly recharge the device.

The docking station may be adapted to incorporate a reference pulse-oximeter as described herein which can then be used for calibration purposes.

According to another aspect of the present disclosure, there is provided a method of measuring blood oxygen levels using a pulse oximetry device, the method comprising:
providing a pulse oximetry device for measuring blood oxygenation, the device comprising:
one or more light emitters for emitting light directed into a human tissue,
at least one light detector for detecting the light emitted from said one or more light emitters after the light has passed through, ie has transited, said human tissue;
measuring one or more characteristics of the detected light which can be converted into corresponding SpO2 measurements;
converting said measured one or more characteristics into said SpO2 measurements based upon calibration data obtained from one or more reference SpO2 values measured using a different, reference pulse-oximeter.

According to another aspect of the present disclosure, there is provided a method of calibrating pulse oximetry blood oxygenation measurements, the method comprising:
providing a first, reference pulse-oximeter adapted to measure reference SpO2 values on the basis of a predetermined pulse oximetry parameter;
acquiring reference SpO2 values during multiple measurements carried out on each of one or more test subjects;
from the reference SpO2 values, obtaining a calibration relationship that expresses SpO2 as a function of the predetermined pulse oximetry parameter;
providing a second pulse oximetry device also adapted to measure said predetermined pulse oximetry parameter;
using the second pulse oximetry device, performing one or more measurements of the predetermined pulse oximetry parameter on a target subject;
converting said measurements into SpO2 measurements using said calibration relationship.

Preferably, the first, reference pulse-oximeter is a medical-grade pulse-oximeter. Preferably, the first, reference pulse-oximeter is medically certified. Preferably, the first, reference pulse-oximeter is as described herein.

The first, reference pulse-oximeter may comprise at least one light emitters and at least one light detector adapted to detect light emitted by said light emitter after the light has passed through a human tissue.

Advantageously, the light detector may be adapted to measure light intensity.

The first, reference-pulse-oximeter may comprise two light emitters for emitting two respective substantially monochromatic lights at different wavelengths as described herein. Further, the predetermined pulse oximetry parameter may be a parameter R as described herein.

Obtaining said calibration relationship from said reference SpO2 values may comprise interpolating said reference SpO2 values. Preferably, said interpolating may comprise linearly interpolating said reference SpO2 values. However, other interpolation curves are in principle possible, depending on the characteristics of the sensors used and/or the physical parameter monitored.

The method may further comprise storing the reference SpO2 values and/or said calibration relationship in a memory provided on the pulse oximetry device.

As a post-calibration optimization procedure, if the method described herein uses a universal calibration relationship derived from tests performed on a plurality of test subjects, the method may further comprise correcting or compensating said reference SpO2 values and/or said calibration relationship as described herein, so that the final SpO2 measurements are optimized for the specific target subject.

The second pulse oximetry device may comprise a bracelet-type pulse oximetry device as described herein.

A case may be provided to accommodate a pulse oximetry unit comprising two light emitters for emitting substantially monochromatic lights at different wavelengths comprising a red wavelength and an infrared wavelength and a light detector. However, a green light may be provided as a replacement of the red light, or in addition to the red and green lights as mentioned hereinabove.

A strap may be provided which may comprise a flexible, elongated element connected to the case.

The method may thus further comprise wearing the second pulse oximetry device to measure the SpO2 measurements around a wrist of the target subject.

Measuring the reference SpO2 values using the first, reference pulse oximetry device may advantageously be carried out for each test subject over a first time period of less than one hour.

Measuring the SpO2 measurements by the second pulse oximetry device may be carried out over a second time period of at least one hour; at least five hours; at least 12 hours; at least 18 hours; or, at least 24 hours.

The method may further comprise categorising the SpO2 measurements according to their values.

The second pulse oximetry device may comprise an accelerometer for measuring levels of activity relating to the target subject.

The method may thus further comprise categorising the adjusted SpO2 measurement according to said levels of activity.

According to another aspect of the present disclosure, there is provided a wearable pulse oximetry device comprising:
- a housing defining a lower face for locating opposite a measurement target area of a target subject;
- at least one pulse oximetry module for performing pulse oximetry measurements;
- an elongated, flexible element connected to the housing for securing the housing on the target subject; wherein
- a projection extends from said lower face and defines a contact surface between the housing and the measurement target area, and
- the pulse oximetry module cooperates with said projection to perform the pulse oximetry measurements.

In a preferred pulse oximetry device, the pulse oximetry module comprises two light emitters disposed within said housing, each light emitter for emitting a substantially monochromatic light, said lights having different wavelengths, and at least one light detector for detecting emitted light reflected to the housing, said at least one detector being also disposed within the housing.

Both light emitters may cooperate with said projection to inject their respective lights into the measurement target area.

The light detector may also cooperate with said projection to detect said reflected light.

The projection may define a projection volume within said housing, and the pulse oximetry unit may be located within said projection volume.

The projection may be part-spherical, such as semi-spherical. However, other shapes are possible.

The lower face of the pulse oximetry device may comprise a friction surface for reducing or inhibiting displacement of the pulse oximetry device on the measurement target area.

Said friction surface may be a side of a double-sided adhesive element.

Preferably the friction surface surrounds said projection, at least partially. Advantageously, the friction surface completely surrounds said projection.

The contact between the contact surface and the measurement target area can therefore be maintained as constant as possible during the calibration and/or measurement phases.

The elongated, flexible element may be in the form of a bracelet, and the housing may be adapted to be worn around a wrist of the target subject.

The wearable pulse oximetry device may further comprise a printed circuit board for operating the device. Said printed circuit board may be located within the housing.

The printed circuit board may comprise, or may operatively be connected to, any one or more of the following:
- a memory;
- a processor;
- a data exchange module, optionally Bluetooth compatible;
- a battery, optionally rechargeable;
- a battery recharge module;
- an accelerometer, optionally triaxial;
- a capacitive switch for detecting contact between the device and the user, the switch being configured accordingly for switching on or off the device.

The pulse oximetry module may be provided as part of, or may be operatively coupled to, the printed circuit board. The light emitters may comprise one or more respective LED elements integrated into said circuit board. The light detector may comprise a photodiode.

The pulse oximetry device may also comprise a feedback feature for providing feedback to the target subject in relation to the SpO2 measurements as described herein. Said visual feedback feature may be adapted to illuminate when at least one of the measured SpO2 values is below a predetermined level. Alternatively, a display may be provided to monitor the SpO2 measurements.

According to another aspect of the present disclosure, there is provided a pulse oximetry system comprising a wearable pulse oximetry device as described herein.

The pulse oximetry system may comprise a docking station as described herein.

The docking station preferably comprises a reference pulse-oximeter as described herein.

The reference pulse-oximeter can then be conveniently used for calibrating the pulse oximetry device as described herein.

According to another aspect of the present disclosure, there is provided a computer programme product comprising a computer readable medium comprising computer readable instructions stored thereon for performing a method as described herein.

According to another aspect of the present disclosure, there is provided a method of taking pulse oximetry measurements, the method comprising:
- providing a first, reference pulse-oximeter adapted to estimate reference SpO2 values from a first, reference PPG signal measured by the reference pulse-oximeter;
- using said first, reference pulse-oximeter, estimating reference SpO2 values for multiple measurements carried out on each of one or more test subjects across a variety of test conditions;
- from the estimated reference SpO2 values, obtaining a calibration relationship that expresses SpO2 as a function of blood oxygenation;
- providing a second, bracelet-type pulse oximetry device adapted to estimate SpO2 values from a second PPG signal measured by the second, bracelet-type pulse oximetry device on the wrist of a target subject;
- using the second, bracelet-type pulse oximetry device, taking one or more measurements of the second PPG signal on the wrist of a target subject;
- converting said measurements into measured SpO2 values using said calibration relationship.

According to another aspect of the present disclosure, there is provided a method of measuring blood oxygen levels using a bracelet-type pulse oximetry device, the method comprising:

providing a pulse oximetry device as described herein, or a system as described herein;

applying the device to the wrist of a test subject such that the one or more light emitters are adapted to emit light into an underside of the wrist, and such that the at least one light detector also detects light from the wrist underside;

measuring one or more characteristics of the detected light which can be converted into corresponding SpO2 measurements;

converting said measured one or more characteristics into said SpO2 measurements based upon said calibration data.

Applying the device to the wrist underside may comprise identifying at least one position of the device relative to the wrist underside which optimises and/or maximises a signal to noise ratio in relation to a PPG signal that represents said measured characteristics of the detected light.

Applying the device to the wrist underside may comprise marking the wrist with reference markers for positioning the device relative to the wrist.

Applying the device to the wrist underside may comprise affixing one side of a double sided adhesive element around a protrusion provided on a backside of the device, wherein said protrusion is arranged to cooperate with the one or more emitters and the at least one detector for emitting and detecting said light and to grip the wrist underside.

Applying the device to the wrist underside may comprise affixing the device to the wrist via the other side of the double sided adhesive element.

Any features described above in connection with any one or more of the aspects of the present disclosure may be included or combined with the features described in connection with any one or more of the other aspects of the present disclosure, unless specifically stated otherwise.

The invention will now be described, purely by way of example, in connection with the attached drawings in which:

DRAWINGS

FIG. 5a shows the underside of the PCB of FIG. 3a;

DESCRIPTION

The inventors have appreciated the advantages of providing upgraded pulse oximetry devices similar to wearable pulse oximetry devices which are soon to become commercially wide spread but adapted to gather medically relevant pulse oximetry data frequently and over extended periods of time, such as full 24-hour cycles, or longer.

The adaptation essentially consists in calibrating such instruments against one or more trusted medical grade pulse-oximeters such as those routinely used in confined and controlled environments, for example hospital rooms, or hospital beds.

The inventors have shown that their unique calibration methodology enables the gathering of more meaningful SpO2 data. Accordingly, it is expected that medical doctors will be able to use these improved data sets to diagnose more easily and/or more reliably conditions which until now have been difficult to diagnose, or that have not been possible to diagnose using conventional pulse oximetry.

The inventors have also improved mechanical aspects of certain wearable pulse oximetry devices, so that these improved devices can maintain a natural, yet appropriate, interface with the measurement area typically located on a back-face or underside of a wrist of a patient (location opposite to that of traditional watches).

Figure 1:
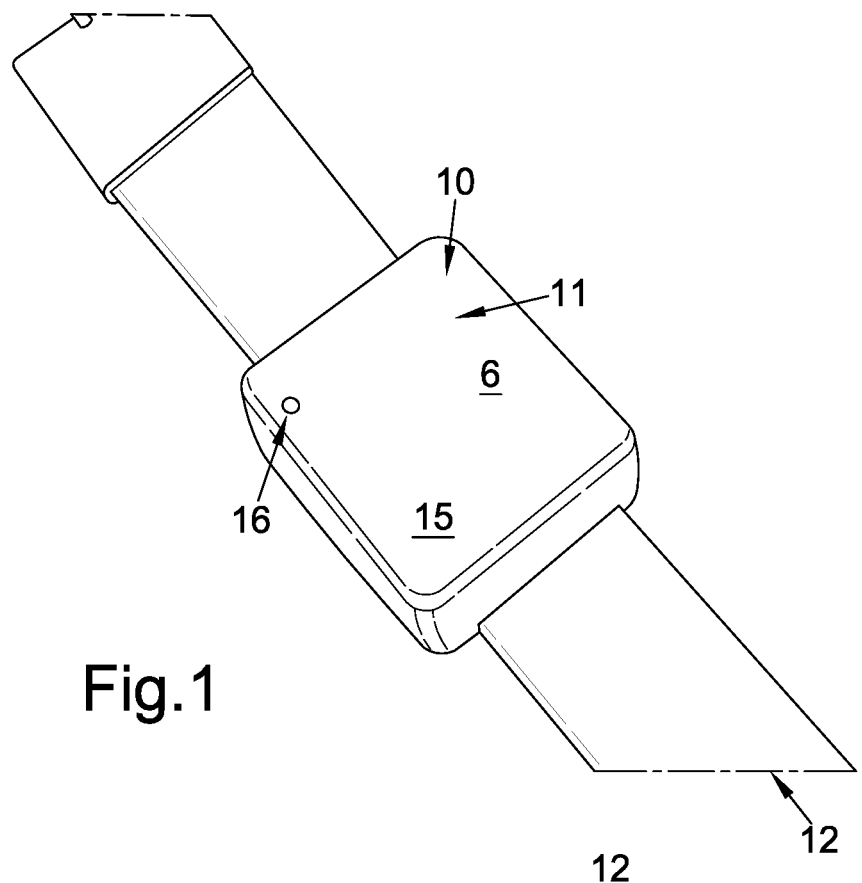
FIG. 1 is a front perspective view of a pulse oximetry device as described herein.

FIG. 1 shows a pulse oximetry device 10 capable of accurately and consistently monitoring levels of oxygen saturation in haemoglobin transported by peripheral arterial blood in a patient—a parameter known from the literature as SpO2.

The pulse oximetry device 10 frequently acquires and monitors medically relevant SpO2 data over relatively large time periods, for example of the duration of 12 or 24 hours.

As used herein, "monitoring" refers to the activity of repeatedly "measuring" and then saving, displaying or otherwise keeping record of SpO2 data over a protracted period of time so as to reveal any trends or patterns. The SpO2 is measured preferably at regular and relatively small time intervals, for example many times per second, or every second, every five or ten seconds, over a period of for example of 12 or 24 hours, as discussed above.

The underlying signal measured by the pulse oximetry device 10 described herein is known in literature as photoplethysmographic signal or, in short, PPG signal. The PPG signal expresses absorption of light that passes through a tissue perfused with arterial blood as a function of time. This depends by a local change in blood volume over time as determined by the systolic and diastolic heart phases. Accordingly, the PPG signal is a generally cyclical waveform and SpO2 is estimated from this periodic signal. The PPG signal can be viewed and analysed in the time and/or frequency domains. It has DC and AC components. Details relating to the PPG signal are not the focus of the present application and will therefore not be described further herein. However, it is noted that the PPG signal is, for the purposes of the present disclosure, the base signal which is made available to the pulse oximetry device 10 by an appropriate pulse oximetry unit 9 (visible in FIG. 2). In particular, the pulse oximetry device 10 described herein uses a light detector 13 as part of such a pulse oximetry unit 9 to detect light intensity.

As is the case more generally with all analogue signals made available by any analogue sensors, the analogue PPG signal detected by the light detector 13 embedded in the pulse oximetry device 10 is sampled and converted into the digital domain according to a predetermined sampling rate. The level of granularity of the acquired data will not be further discussed herein. Instead, the digitally acquired waveforms will simply be treated and referred to herein as one or more signal acquisitions. SpO2 can be measured each time over one or more acquisitions, of variable time duration.

Before SpO2 is extracted, the acquisition(s) can be conditioned according to one or more known techniques such as filtering, averaging or the like. However, these details are not relevant to the purpose of the present description. Instead, it is noted that SpO2 can be extracted more or less frequently from acquisitions having different duration and that may be conditioned according to different techniques. For example, the PPG signal may be acquired over 10 seconds, after different intervals, and averaged within these acquisition windows. Otherwise, the PPG signal may be acquired over moving windows of 10 seconds and filtered within these windows. A corresponding SpO2 measurement can then be performed by the instrument. Alternative processing methods are however possible. Further, the signals can equally be processed in the time and/or frequency domains, as convenient.

The SpO2 measurements described herein are derived from one or more measured physical parameters. In the present description, SpO2 is estimated from a measured intensity of light that has not been absorbed by oxygenated blood and which, therefore, can complete its travel to the light detector 13. The light absorbed by oxygenated blood relates directly to the quantity of oxygen transported by the blood. If all the haemoglobin transported by the blood transports oxygen, then SpO2 is equal to 100%.

As mentioned above, the quantity or volume of blood (and, with it, of haemoglobin) at any one time present in an area of the human body made the target of the SpO2 measurements generally cycles in time depending on the heart cycles and is therefore related to the heart rate. Generally, however, the blood volume present in the target area at any given time also depends from various other biometric parameters (for example breathing rate or body temperature) or patient conditions (for example physical activity), etc. It is for these reasons—in combination with a weaker PPG signal—that the measurement of SpO2 at the wrist is a challenge, which the present inventors have addressed.

Returning now to the device 10 of FIG. 1, the device 10 can essentially be described as a pulse oximetry bracelet that includes a case 11 and a strap 12. The case or housing 11 accommodates a pulse oximetry unit 9 which, as discussed above, in the presently described examples includes a light detector 13. The case 11 is divisible in two parts, of which the front portion 15 is that visible in FIG. 1. A red LED light 16 extrudes from the front face 6 of the case 11, and, as it will be explained in further detail below, provides visual feedback to the patient. As it will be appreciated, the device 10 is very similar at least in shape to a traditional watch. However, the case 11 may be worn on the underside (or back-face) of the wrist, in position circumferentially substantially opposite to that of a traditional watch.

Figure 2:
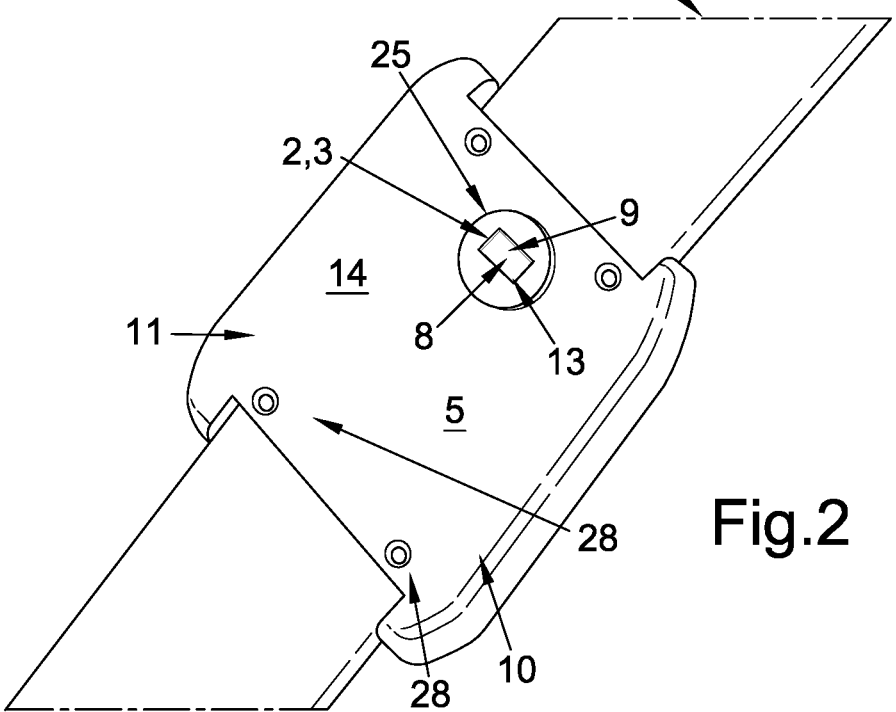
FIG. 2 is a rear perspective view of the pulse oximetry device of FIG. 1.

FIG. 2 shows the rear portion 14 of the case 11. The light detector 13 is disposed on the rear face 5 of the case 11 as shown in FIG. 2. The light detector 13 is associated, in the described pulse oximetry device 10, to two light sources 2, 3 adapted to illuminate the skin of the patient subject to the tests. The light detector 13 is adapted to pick up light reflected or scattered back to the device 10 after the light has travelled through the wrist of the patient at depths of typically a few millimetres.

Figures 3A, 3B:
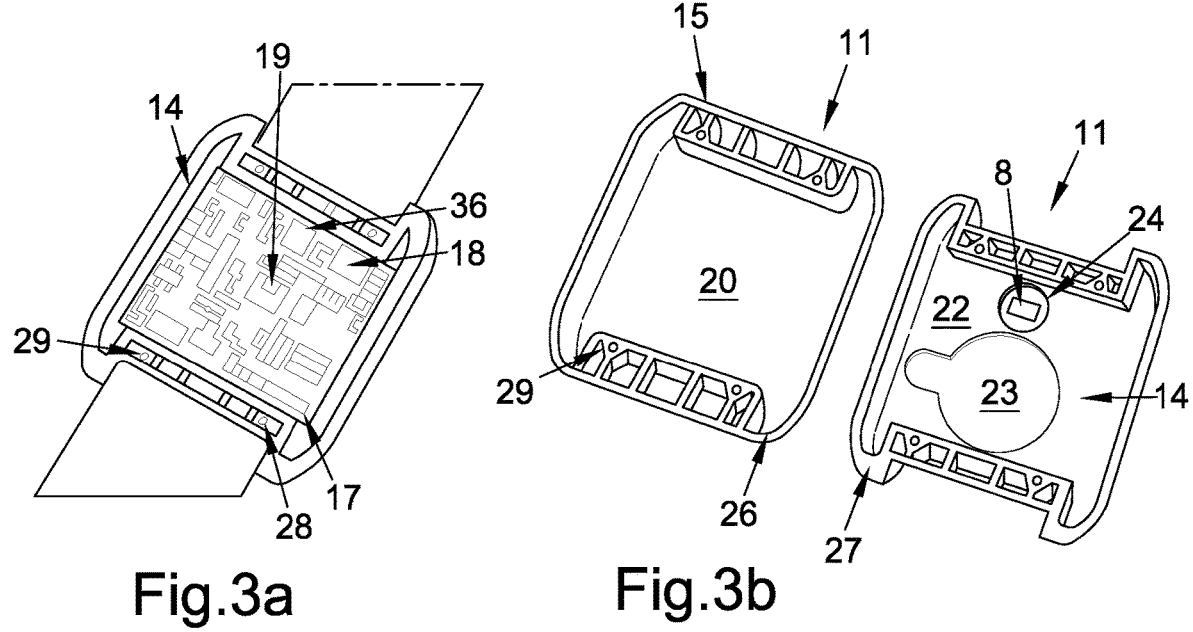
FIG. 3a is a front perspective view of the pulse oximetry device of FIGS. 1 and 2 with an upper portion of a case removed to reveal a printed circuit board (PCB) that is used to control the device.
FIG. 3b shows the internal faces of the upper and lower portions of the case of the pulse oximetry device of FIGS. 1-3, with the PCB and other components removed.

FIG. 3*a* reveals details of a printed circuit board (PCB) 17 housed in the case 11. The PCB 17 includes various modules that enable the pulse oximetry device 10 to perform different functions. As also seen in FIG. 3*a*, a memory 18 and a processor 19 are integrated on the PCB 17. The PCB 17 thus manages the acquisition of the PPG signal from the light detector 13 from which the SpO2 is estimated as further described below.

Figure 4:
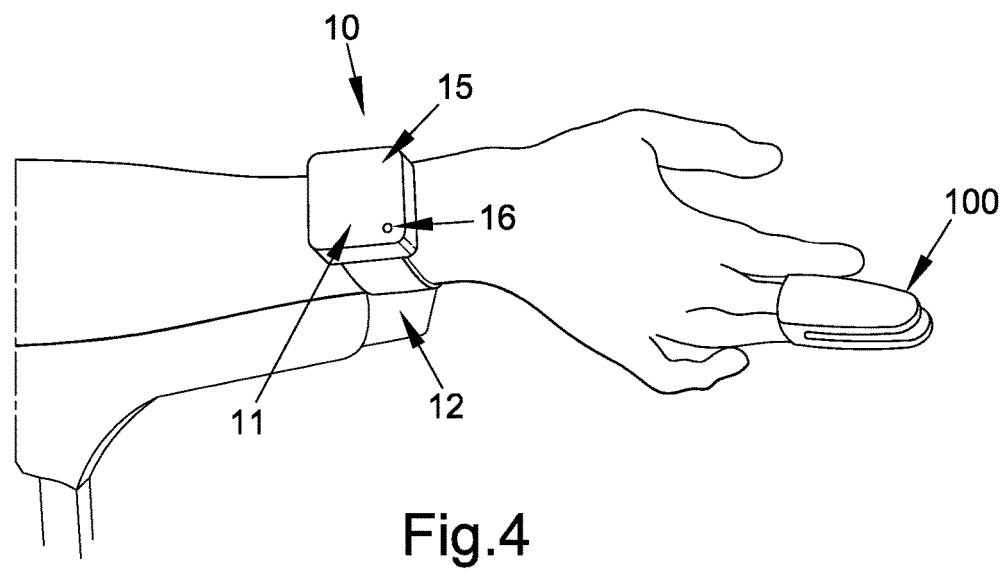
FIG. 4 shows the pulse oximetry device of FIGS. 1-3 during a calibration procedure that utilises a known medical grade pulse-oximeter with a finger clip probe as a reference instrument.
Figure 5A:
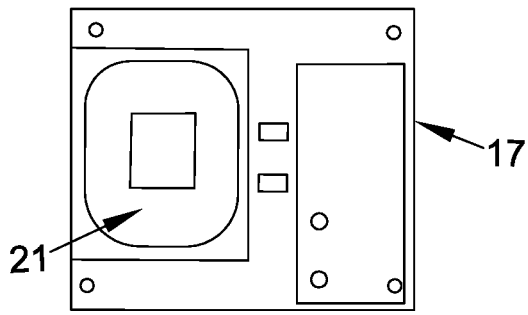

FIG. 3*b* shows the front and rear portions 15, 14 of the case 11 one next to the other to reveal additional constructive details of the case 11. The front portion 15 of the case 11 has an inner side or face 20 that faces, in use, the PCB 17. The rear portion 14 of the case 11 is instead profiled to accommodate and support a recharge coil 21 (shown in FIG. 5*a*). In particular, an inner face or side 22 of the rear portion 14 of the case 11 comprises a first recess 23 shaped to conform to this coil 21. The recharge coil 21 is mounted on the rear side of the PCB 17 as shown in FIG. 5*a*. A second recess 24 is also identifiable on said inner face or side 22 of the case 11. This recess 24 when seen from outside defines a projection 25 of the underside 5 of the case 11 that projects to contact the skin on the wrist of the patient, as shown in FIG. 4. The recess 24 accommodates the pulse oximetry module or unit 9 that comprises the light detector 13 and the light sources 2, 3. The external projection 25 has a window 8 adapted to transmit light therethrough.

The pulse oximetry unit 9 mounted on the device 10 is, in the described pulse oximetry device 10, type MAX30102 manufactured by Maxim Integrated, Inc. However, in alternative devices 10 different pulse oximetry units 9 may be used, for example provided by different makers, or having different light emitter and/or sensor configurations.

Another characteristic of the described device 10 is that the device 10 is battery-operated. However, the battery has not been shown in the drawings for clarity purposes, so that other components are better visible. The battery will not be described further.

As will be appreciated, power consumption of this type of devices 10 is minimal. The light sources or emitters 2, 3 embedded in the pulse oximetry unit 9 are LED type and emit red and infrared lights of wavelengths of approximately 600 and 900 nm, respectively.

The projection 25 optimises the contact between the device 10 and the skin of the subject at the wrist, when the device is in use or is being calibrated, as shown in FIG. 4 and as further described below. The protrusion 25 in other words is capable of locally increasing the force and pressure exchanged between the wrist and the case 11, so as to provide additional grip and stability.

Figure 6:
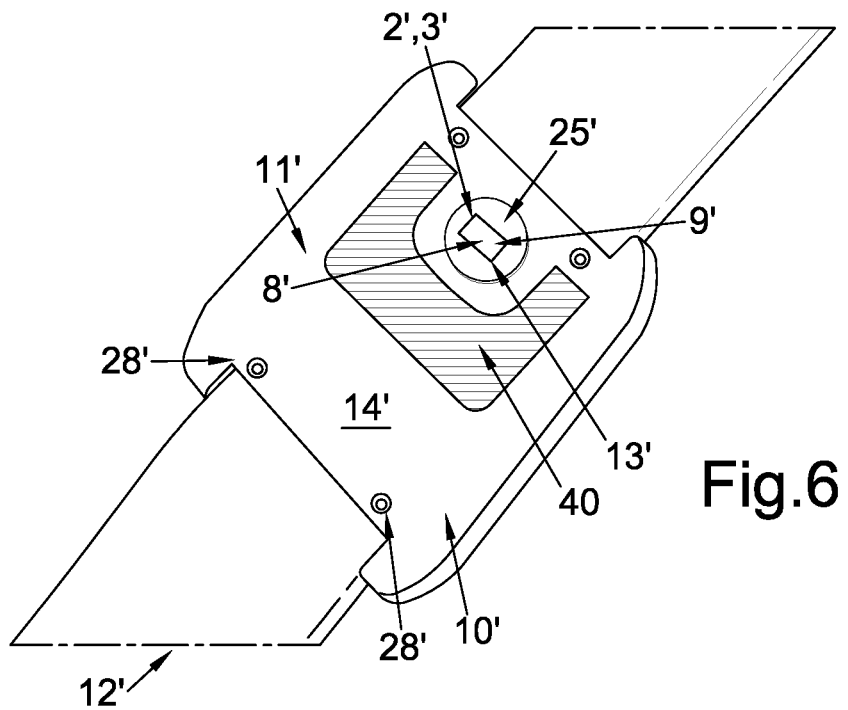
FIG. 6 is a rear perspective view of a second pulse oximetry device having a friction insert.

The pulse oximetry device 10' of FIG. 6 is similar to that shown in FIGS. 1-3 except that it in addition incorporates a rubber insert 40 on the rear face 5' of the lower part 14' of the case 11'. This makes the device 10' less likely to become displaced on the target measurement area. Accordingly, this arrangement provides improved contact between the projection 25' of the device 10' and the wrist of the patient. This improves the consistency of the SpO2 measurements. Numerals corresponding to the numerals adopted in FIGS.

1-5 have been adopted in connection with this pulse oximetry device 10', with the addition of an apex to denote equivalent features described in connection with the earlier device. The rubber insert could alternatively be a double sided adhesive element which is first installed on the device, then attached to the skin.

The device 10 is water proof and this property is provided by water proofing matching profiles 26, 27 of the upper and lower portions 15, 14 of the case 11, and by their connection by means of four screws 28 disposed on the rear face 5 of the lower portion 14 of the case 11 which are used to close the two parts 14, 15 of the case 11, as shown in FIG. 2. However, it will be appreciated that in other devices not described herein in detail these constructive particulars may change. These screws 28 are coupled to appropriate bores 29 provided on the inner face 20 of the upper portion 15 of the case 11, as shown in FIG. 3*b*. Corresponding screws 28' are also visible in the device 10' shown in FIG. 6.

Figure 5B:
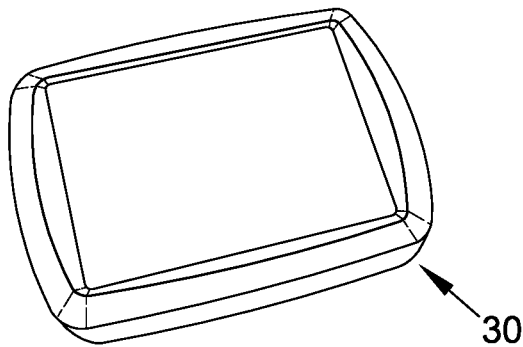
FIG. 5b shows a docking station for the pulse oximetry device of FIGS. 1-4.
Figure 5C:
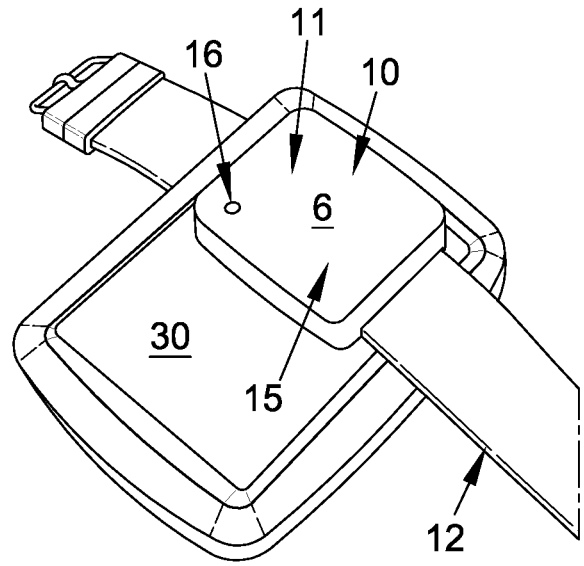
FIG. 5c shows the pulse oximetry device docked to the docking station of FIG. 5b.

The PCB 17 can communicate any data stored in the memory 18 via a Bluetooth wireless module (also not shown). The data can be transferred to a docking station 30, a personal computer and/or to the Cloud, depending on the application. In preferred applications, SpO2 measurements gathered by the pulse oximetry device 10 are stored in the memory 18 and periodically downloaded to the docking station 30. The docking station 30 then periodically downloads the data to a personal computer or the Cloud. FIGS. 5*b* and 5*c* show the docking station 30 for use with the device 10. The docking station 30 is in addition used to recharge wirelessly the onboard battery via the recharge coil 21, as known in the arts. Preferred docking stations (not shown) incorporate the reference pulse-oximeter 100, which is use to calibrate the main pulse oximetry device 10 as described herein.

The described pulse oximetry device 10 also includes a triaxial accelerometer 36 (see FIG. 3*a*) which can track movements of the patient to infer patient's behaviour. In the described pulse oximetry device 10, the accelerometer has a 10-bit vertical resolution and is manufactured by NXP Semiconductors. Alternative models and makes would however be possible.

In addition to SpO2, the device 10 is capable of measuring heart rate (also from the PPG signal). Using the accelerometer 36 and the information on the heart rate it would be possible, for example, to estimate a distance walked by the subject, according to algorithms known in the art but not described herein.

Alternatives or additions to the accelerometer 36 are possible, for example in the form of a GPS system which could be fitted to the device 10. The device 10 could thus not only recognise basic events such as 'patient walking' or 'patient jogging', but it could also further characterise the activity of the subject wearing the device 10, for example on the basis of GPS coordinates. Accordingly, the wearable pulse oximetry bracelet 10 described herein not only can record oxygen desaturation events, but it can also quantify their duration and intensity in relation to the activity of the subject.

The processor (or microcontroller) 19 oversees the overall functioning of the device 10. In particular, the processor/microcontroller 19 will:

1) Trigger the emission of light from the light emitters 2, 3—this will ensure the presence of a PPG signal;
2) Acquire the PPG signal, which, as discussed above represents a light intensity and which, in the present description, represents the intensity of light reflected back to the pulse oximetry unit 9 and detected by the light detector 13 ('reflection mode');
3) Condition the PPG signal, if necessary and/or as prescribed;
4) Calculate SpO2 on the basis of the PPG waveform or waveforms captured by the pulse oximetry device 10. Each SpO2 measurement will be associated to an absolute or relative time at which it was taken. Note that, in simpler terms, it is possible to refer to this phase as the 'measurement' of SpO2 although, as previously explained, this is rather a calculation or estimation, or in yet other words an indirect measurement;
5) Memorise the measured SpO2 values in memory 18;
6) Download the measured SpO2 values to the docking station 30 or other device, as specified;
7) Manage the initial configuration of the pulse oximetry device 10;
8) Manage any additional function buttons (not shown) that may be provided with the device 10; and,
9) Manage the energy available in the battery, including providing for any power saving modes.

The PCB 17 was sourced from Microchip Technology Inc. with embedded microprocessor 19 and storage memory 18. However, other makes and/or architecture are possible although are not described here in detail.

The microprocessor 19 has 16-bit vertical resolution, 128 KB of serial FLASH memory and 16 KB of RAM memory embedded.

The storage memory 18 is a serial FLASH memory of 8 MB.

Other microprocessor capabilities and/or memory sizes could however be appropriate, depending on the application and/or performance requested.

The Bluetooth capability of the communication module (not shown) of the PCB 17 allows the device 10 to communicate with the docking station 30 as well as other Bluetooth enabled devices. An app may be envisaged to manage said data exchange processes.

SpO2 measurements obtained from a non-calibrated pulse oximetry device 10 of the type shown in FIGS. 1-3 have been shown to be only loosely in line with those obtained by a traditional, certified medical pulse-oximeter 100 such as that shown in FIG. 4. This can be addressed with the calibration procedure that will now be described.

Figure 9:
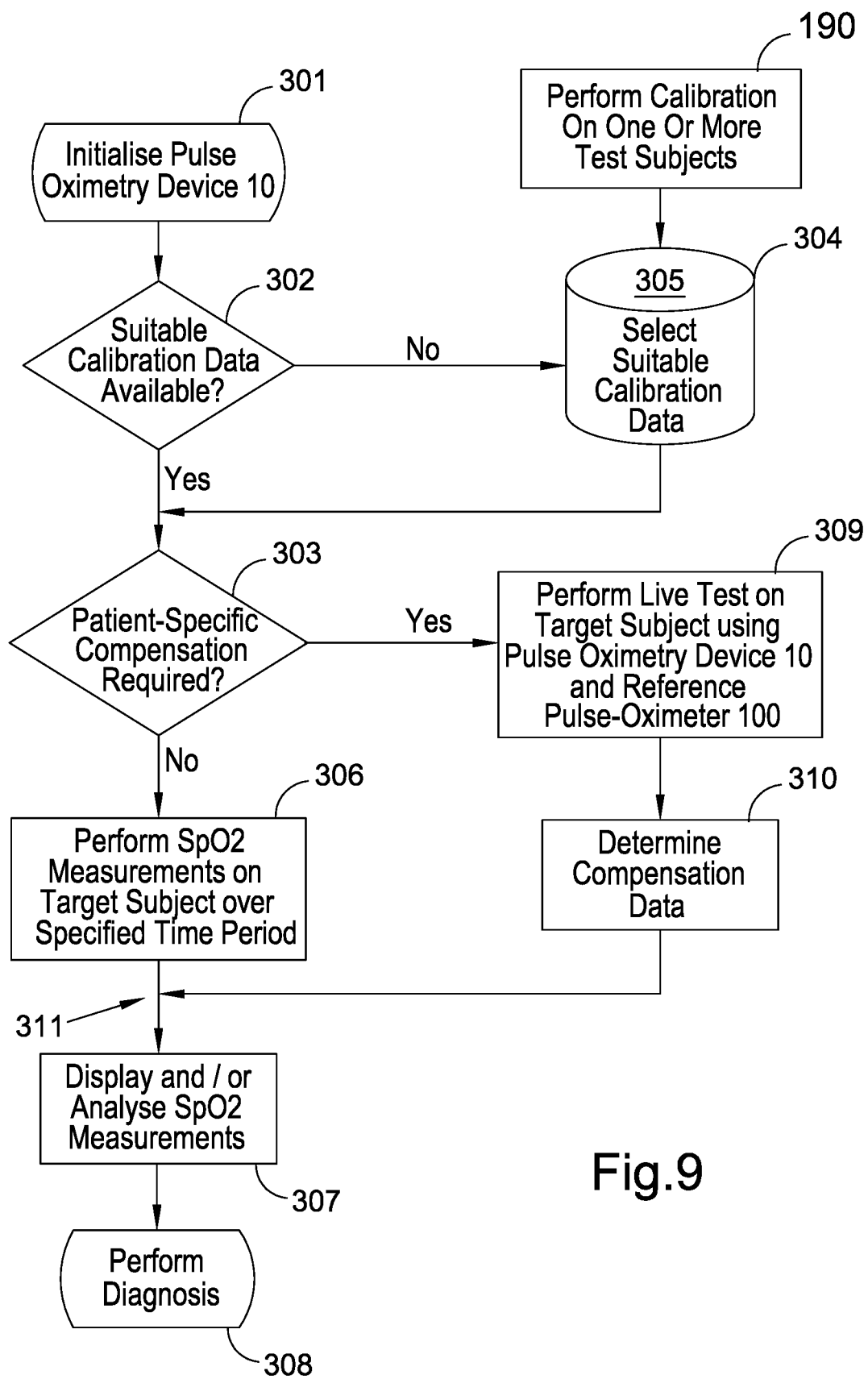

FIG. 4 illustrates the general principle of the proposed calibration method 190 (also represented in FIG. 9). The wearable pulse oximetry device 10 of FIGS. 1-3 is calibrated against a medically graded pulse-oximeter 100 of conventional construction. The inventors have appreciated that by adopting this calibration procedure 190 the wearable pulse oximetry device 10 can measure SpO2 data of at least comparable quality with respect to those produced by the medical-grade pulse-oximeter 100. However, the advantage of the present bracelet-type pulse oximetry device 10 is that it is better suited than any traditional medical-grade pulse-oximeter 100 to monitor non-invasively and non-obstructively SpO2 during extended time windows, for example of the duration of many hours or days.

The calibration procedure 190 described herein was conducted on a test group of four subjects. However, it will be observed that the calibration procedure 190 is not so limited and fewer or more test subjects could have been chosen. Further, as it will be apparent from FIG. 9 described in more detail below, the calibration process 190 can in principle be carried out or repeated at any time and/or in preparation for any specific applications with an increased number of test subjects, or with different test subjects. Increasing the number of test subjects, or changing the test subjects, is believed to improve the quality of the final SpO2 measurements, for reasons that will be apparent from the description below.

During the tests carried out on the four patients, an SpO2 measurement frequency of one measurement every 10 seconds has been adopted. However, it will be appreciated that this is just an example and different measurement frequencies could have been used. The acquired data were memorized in the pulse oximetry bracelet 10 to represent a time period of up to 24 hours. The data were then transferred from the pulse oximetry device 10 to the docking station 30. This is just an example, since the data could have equally been transferred to a PC, or from the docking station 30 to a PC, prior to processing and display and/or analysis.

For each subject, the device 10 was positioned on the left wrist in the position shown in FIG. 4. To make sure that the device 10 could pick up an appropriate PPG signal we checked that the peak amplitude of the infrared signal was at least 100 units through the software interface MAX30102 EV kit provided by Maxim Integrated, Inc. together with the pulse oximetry unit 9. The location of the sensor can be adjusted on the backface of the wrist until a reasonable, optimum or maximum signal is detected.

In order to obtain reference measurements of SpO2, each subject also wore on the left index finger a Nonin medical grade pulse oximetry device model 2500A, used herein as the reference pulse-oximeter 100. Measurements of SpO2 (and heart rate) were thus available from this medical grade reference device 100 as well as from the device 10 to be calibrated. It is observed that while the medical grade reference device 100 performed measurements in 'light transmission' mode, the pulse oximetry device 10 undergoing calibration operated in 'light reflection' mode. Whilst this is the case in the described calibration procedure 190, alternative calibration procedures may encompass alternative devices 10, 100 and different combinations of operations modes, including 'mixed' operations modes (ie wherein the light detected may have been partly transmitted and partly reflected before it is detected in the form of the PPG signal).

Further, in the described calibration procedure 190, the devices 10, 100 inferred SpO2 on the basis of the same parameter R evaluated from the detected light. The formulation of R is provided below. However, it will be appreciated that the proposed calibration procedure 190 is in principle independent from the actual parameters evaluated by the specific devices 10, 100 used in the process 190. The concept underlying the present disclosure is that of calibrating a wearable pulse oximetry device 10, such as the bracelet-type pulse oximetry device 10 described herein, against a medical-grade reference pulse-oximeter 100 such as the Nonin device used herein, independently from how each instrument actually evaluates SpO2.

Returning to the tests, subjects 1, 3 and 4 were asked to remain seated, breathe initially in a normal way, keep a left arm at rest (motionless, but sufficiently firm) and follow the protocol described below:
 a. 2-3 minutes of normal breathing;
 b. Apnea for as long as possible;
 c. 3-4 minutes of recovery time with normal breathing;
 d. Apnea for as long as possible;
 e. 2-3 minutes of recovery time with normal breathing.

Subject 2, who was an asthma sufferer, was asked to breathe normally while a mask administered a gaseous mixture with oxygen up to 60%.

For each test subject, the following experimental data were acquired by the light detector 13 of device 10:
 the intensity of the reflected infrared light as a function of time (ie infrared waveform); and,
 the intensity of reflected red light as a function of time (ie red waveform).

The above signals together represent the PPG signal in the described set-up. In alternative set-ups, at least in principle, only one signal could be used insofar as the underlying light is sufficiently affected by absorption in connection with oxygen transported by hemoglobin as it travels the target blood-perfused tissue.

Further, the acceleration of the pulse oximetry device 10 as measured by the triaxial accelerometer 36 according to each of three reference axes Ay, Ax and Az was also recorded.

Using the reference pulse-oximeter 100, SpO2 was also recorded as a function of time in correspondence with the measurements taken by the pulse oximetry device 10, which was the device being calibrated.

All the data acquired from the pulse oximetry device 10 were eventually stored on a PC, and the corresponding waveforms processed to provide input to a mathematical algorithm (know in the art) to calculate the SpO2, thus simulating on the PC the processing and calculation of parameters which in real life would be done by the onboard microcontroller 19 of the device pulse oximetry 10.

The measurements of SpO2 achieved by the reference pulse-oximeter 100 were plotted against the corresponding values of the parameter R achieved by the pulse oximetry device 10 undergoing calibration.

R is mathematically calculated from the amplitude of the continuous (DC) and alternating (AC) red and infrared components of the reflected light signals acquired by the pulse oximetry device 10 as follows:

$$R = \frac{RedAC/RedDC}{InfraRedAC/InfraRedDC}. \quad \text{Equation 1}$$

Figure 8:
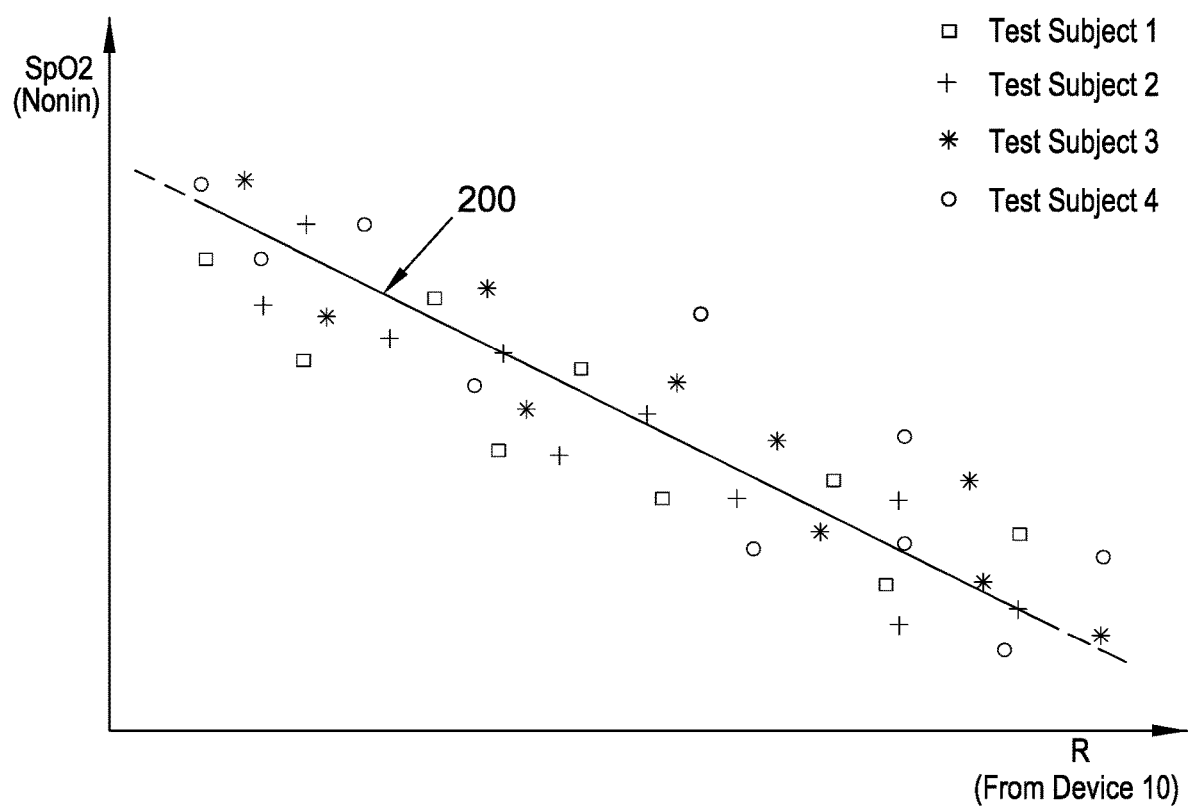
FIG. 8 is a graph illustrating the derivation of a calibration curve for the pulse oximetry devices of FIGS. 1-6; and, FIG. 9 is a flow chart illustrating steps for performing acquisition and monitoring of SpO2 measurements as described herein, and follow-on diagnosis.

A merely illustrative graph is shown in FIG. 8, for each of the four tested patients.

In the described calibration procedure 190 illustrated (purely schematically) by FIG. 8, the calibration curve 200 was obtained by linear interpolation of the plotted data pairs. In the calibration scenario 190 described herein, this corresponded to Equation 2 given below:

$$SpO2 = -39.4R + 112.9. \quad \text{Equation 2:}$$

Once calibrated according to the above Equation 2, the measurement of SpO2 on the pulse oximetry device 10 are performed accordingly. Equation 2 therefore expresses a single linear relation between SpO2 and the measured parameter R which was obtained experimentally as a calibration relationship for the device 10 on the basis of the four test subjects and the reference pulse-oximeter 100.

The quality of the heart rate measurement using the pulse oximetry device 10 was assessed by measuring an error as the standard deviation percentage calculated between the values obtained from the infrared and red waveforms acquired with the pulse oximetry device 10 and corresponding records performed on the same subject with the reference medical pulse-oximeter 100. The results were considered to be within acceptable error boundaries.

In order to recognize any events of hypoxia and to classify them correctly on the basis of their severity, the SpO2 data obtained from the calibrated device 10 were subsequently input to a classification algorithm that was built in accordance with the rules described hereinbelow.

Starting from values which expressed SpO2 as a percentage, the following colour groups were used to evaluate the severity of the events:

Green or class 1: SpO2>93%;
Yellow or class 2: SpO2 between 88% and 93%;
Orange or class 3: SpO2 between 83% and 88%;
Red or class 4: SpO2<83%.

An exemplary summary table is provided below:

TABLE 1

| | Total recorded time | Rest conditions, during the day | Rest conditions, at night | Presence of physical activity |
|---|---|---|---|---|
| Green SpO2 ≥ 93% | XX % HH:MM:SS | XX % HH:MM:SS | XX % HH:MM:SS | XX % HH:MM:SS |
| Yellow 88% ≤ SpO2 < 93% | XX % HH:MM:SS | XX % HH:MM:SS | XX % HH:MM:SS | XX % HH:MM:SS |
| Orange 83% ≤ SpO2 < 88% | XX % HH:MM:SS | XX % HH:MM:SS | XX % HH:MM:SS | XX % HH:MM:SS |
| Red SpO2 ≤ 83% | XX % HH:MM:SS | XX % HH:MM:SS | XX % HH:MM:SS | XX % HH:MM:SS |
| Total time | HH:MM:SS (100%) | HH:MM:SS (XX %) | HH:MM:SS (XX %) | HH:MM:SS (XX %) |

According to table 1, the SpO2 measurements were categorised according to their classes and according to three basic conditions that describe in broad terms the level of activity of the patients (rest during the day, rest at night and physical exercise), as inferred from the acceleration measurements obtained from the accelerometer 36. The duration of these events is provided in each window. Each window corresponds to one of the above classes and one basic patient condition.

The categorisation of the SpO2 measurements showed a satisfactory degree of consistency between the calibrated pulse oximetry device 10 and the reference pulse-oximeter 100.

Optimization Method

An optimisation method 309, 310, 311 is now described. This method is also labelled in FIG. 9 which is described further below. The optimisation method can further enhance the SpO2 measurements obtained from a calibrated pulse oximetry device 10.

The accuracy of the SpO2 measurements recorded using the bracelet-type pulse oximetry device 10 can be optimised, for each patient, by calculating an average of the SpO2 values measured by the reference pulse-oximeter 100 and by utilising this average to compensate a corresponding averaged value of SpO2 measured by the pulse oximetry device 10.

The inventors have recognised that this patient-specific optimisation procedure 309, 310, 311 can be beneficial to the quality of the measurements prior to recording SpO2 levels over extended time periods using the pulse oximetry device 10. We refer interchangeably in the present description to 'optimisation', 'correction' and/or 'compensation' of existing calibration data.

In other words, the 'dynamic' response of the device 10 is inferred from the calibration procedure across many patients and a variety of potential conditions. The 'baseline' is instead recognised to be patient-specific.

To validate the proposed calibration compensation procedure 309, 310, 311, the data produced by the pulse oximetry device 10 were all compensated and then compared with the results obtained with the reference device 100. The results were satisfactory.

In the calibration procedure 190 described above, SpO2 was estimated for each measurement on the basis of a linear regression calibration curve 200 that relates the SpO2 estimated using the reference device 100 and the parameter R calculated from the recorded signals with the pulse oximetry device 10. In the described calibration procedure 190, the experimental relationship between R and SpO2 was linear and defined by the below:

$$SpO2 = MR + Q, \quad \text{Equation 3}$$

where M and Q are coefficients obtained experimentally on the basis of the calibration measurements performed on multiple subject (these are schematically plotted in FIG. 8).

The inventors have realized that the above coefficients vary slightly from subject to subject. Equation 2 was derived to express a generalized or universal relation that links R and SpO2 for the device 10. This generalized relationship was taken as a calibration curve applicable to any target subjects on which SpO2 measurements are to be taken.

To optimize the estimation of SpO2 on the target subjects, the initial value of SpO2 measured with the reference pulse-oximeter 100 was saved and subsequently used to offset the measurements obtained with the pulse oximetry device 10. In this way, the measurement of SpO2 performed by the reference pulse-oximeter 100 on the finger served to determine a value of a patient-specific correction which would improve the accuracy of the final measurements by compensating for patient-specific characteristics such as, for example, the different characteristics of the skin between one subject and another.

On the phalanx or forefinger it is possible to measure PPG signals of greater intensity and hence it is possible to estimate SpO2 with an accuracy greater than on the wrist, where, instead, in the case of the present pulse oximetry device 10 the IR and RED PPG signals are weaker and thus more affected by noise and artefacts.

In order to validate the optimization technique 309, 310, 311 described above using further sets of experimental acquisitions, it is proposed to carry out the following work plan:

1. Repeat the calibration procedure 190 on a larger group of test subjects with different characteristics (sex, age, skin, pigmentation, etc.);
2. Derive a new general or universal relation 200 according to Equation 2 and use the M and Q parameters so derived to evaluate a predicted error on each of the SpO2 records concerned;
3. Compensate the measured SpO2 values with the optimization procedure described herein and evaluate an error on the SpO2 measurements after compensation; and
4. Compare the two techniques (with or without compensation) for measuring SpO2 to determine and quantify any improvement obtained.

In a practical clinical application, a correction value in accordance with the optimization method described herein can be obtained by asking the patient to wear a first pulse oximetry device 10 as described herein, waiting 2-3 minutes for the adaptation of the skin to the pressure exerted by the device 10, then performing measurements of SpO2 with the device 10 and with a second, reference pulse-oximeter 100 applied on the index finger of one hand. This second, reference pulse-oximeter 100 can preferably be integrated into the docking station 30.

To validate the proposed technique, the experimental data captured during the tests described above have been used to simulate any improvements which could be obtained by applying the present optimisation method 130, according to the following routine:

1. We considered the acquisition time windows for all test subjects from the 60th second to the $150^{th}$ second;
2. For each time window, and for each test subject, we averaged the SpO2 measurements obtained with the reference medical device 100 (|SpO2Refl);
3. For each time window, and for each patient, we averaged the SpO2 measurements obtained from the calibrated pulse oximetry device 10 (|SpO2Dev|);
4. We then calculated an offset between the two measurements as:

offset=|SpO2Dev|−|SpO2Ref|;   Equation 4:

5. The SpO2 measured from the calibrated pulse oximetry device 10 was optimised according to the equation:

SpO2Opt=SpO2Dev−offset.   Equation 5:

wherein SpO2Opt is the optimized measurement.

After the above offset was applied to the SpO2 values measured with the device 10, the results were used again in the classification algorithm described above in relation to Table 1, with substantial quality improvements of the clinical assessment.

FIG. 9 is a flow chart that illustrates a procedure for achieving diagnosis based on the measurements of medical grade SpO2 values using a calibrated pulse oximetry device 10 as described herein. Accordingly, FIG. 9 provides the context of the calibration procedure 190 and for the optimization procedure 309, 310, 311 described above.

The pulse oximetry device 10 initially undergoes initialisation 301, which may comprise operations known in the art such as checking that the battery of the device 10 is sufficiently charged and that the memory 18 is sufficiently free to store the required data.

The operator then decides 302 whether any existing calibration data are appropriate for the intended clinical application.

If the pulse oximetry device 10 is adequately calibrated, then in the next step 303 the operator decides whether any patient-specific compensation of the to-be-acquired SpO2 measurements is required. This is for example the case when the pulse oximetry device 10 uses a generalized or universal calibration curve 200 of the type discussed herein. However, it may be the case that patient-specific compensation is not required. This happens when the pulse oximetry device 10 is already programmed with a patient-specific calibration curve. For test subjects 1 to 4 referred to in FIG. 8, such a calibration curve would be expressed for each subject according to Equation 3, on the basis of the respective calibration tests, with the coefficients M and Q being thus patient-specific.

If patient-specific compensation is not required, then the pulse oximetry device 10 can be provided to the target subject who wears it for an agreed time period while the pulse oximetry unit performs the required measurements. The pulse oximetry device 10 first measures the parameter R and, then, converts these R values into corresponding values of SpO2 on the basis of the calibration data loaded on the pulse oximetry device 10. This is exemplified by block 306 in FIG. 9.

Figure 7:
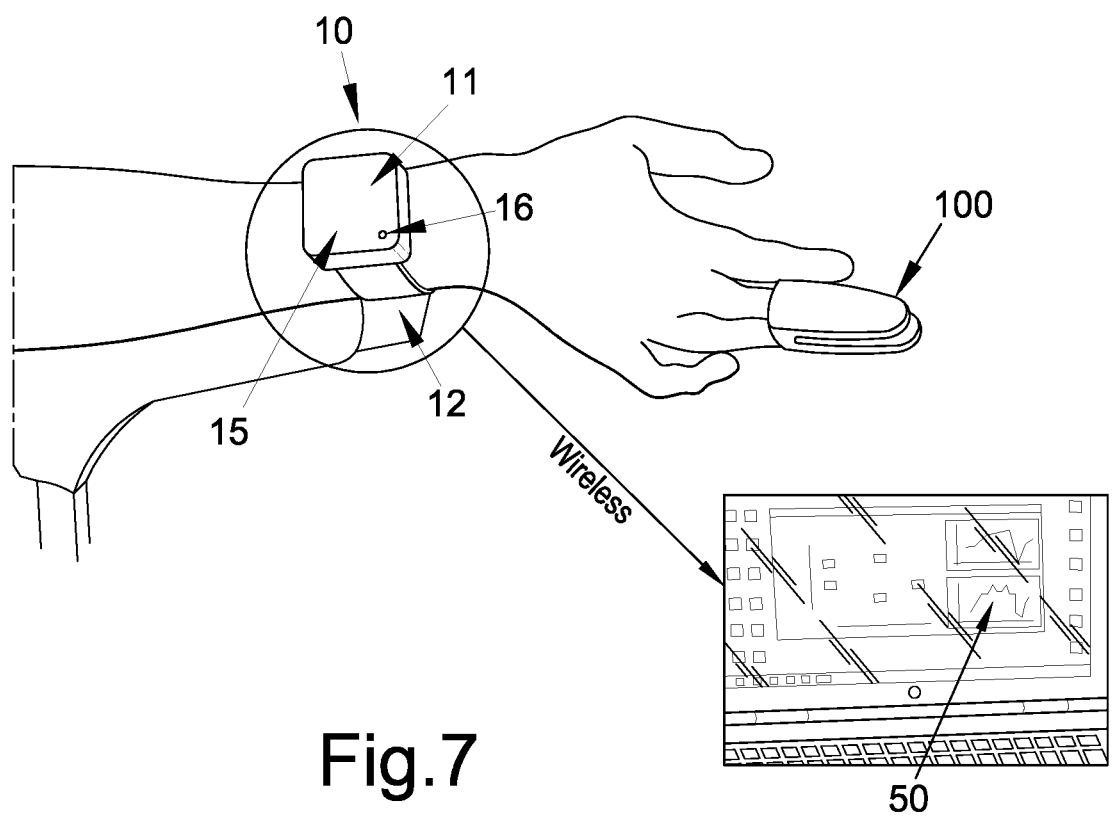
FIG. 7 illustrates a process of monitoring blood oxygenation levels on a patient.

The data acquired are then displayed on a display 50, for example such as the one shown in FIG. 7 and/or they are then analysed. This step is represented in FIG. 9 by block 308.

If the pulse oximetry device 10 is not adequately calibrated for the proposed clinical application, then the operator has a choice of consulting a database 305 to select an appropriate calibration curve. This is represented in FIG. 9 by step 304.

The calibration curves are divided in the database 305 into calibration libraries each referring to one or more test subjects categorised according to certain characteristics such as sex, age group, race, etc. The calibration libraries can include new calibration curves obtained with the calibration procedure 190 described herein and from time to time uploaded to the database 305.

Another way of classifying the calibration curves is, for example, based on the type of pulse oximetry unit 9 and/or pulse oximetry device 10 used to take the measurements, and/or on the basis of the reference pulse-oximeter 100 used to obtain the calibration curves. In this way, the operator ensures that the selected calibration curve is for the correct pulse oximetry device 100 and refers to a desired reference pulse-oximeter 100. In the lack of information on the clinical application, a generalised calibration relation can be used of the kind expressed by Equation 2 above.

If a generalised calibration relationship is used, then the operator may decide 303 that patient specific compensation is advisable and/or required. A 'live' test can then be performed (step 309) on the target subject using the pulse oximetry device 10 and an appropriate reference oximeter 100, as described above. The SpO2 measurements obtained in this live test can then be used to derive one or more compensation parameters (step 310), also as described above. Finally, the compensation parameters can be used to alter the SpO2 measurements after that these have been taken (junction 311).

The resulting diagnosis 308 is provided on data sets which are more accurate and/or more consistent with respect to the prior art. Further, these SpO2 data are taken using the pulse oximetry device 10 over large time periods while the target patient carries out normal daily activities. This further enhances the probability to achieve correct diagnosis.

The following numbered paragraphs also form part of the present disclosure:

1. A pulse oximetry device for measuring blood oxygenation, the device comprising:
   one or more light emitters adapted to emit light directed into a human tissue;
   at least one light detector for detecting the light emitted from said one or more light emitters after the light has passed through said human tissue;
   wherein the device is adapted to convert one or more measured characteristics of the detected light into corresponding SpO2 measurements,
   wherein said conversion is based upon calibration data obtained from a plurality of reference SpO2 values measured using a different, reference pulse-oximeter.

2. A pulse oximetry device according to numbered paragraph 1, wherein said device is adapted to measure a light intensity; or,
   wherein said one or more measured characteristics comprise a light intensity.

3. A pulse oximetry device according to numbered paragraph 1 or 2, comprising two light emitters for emitting two respective substantially monochromatic lights at different wavelengths.

4. A pulse oximetry device according to numbered paragraph 3, wherein said different wavelengths comprise a red wavelength and an infrared wavelength.

5. A pulse oximetry device according to numbered paragraph 2, 3 and 4, wherein the device is adapted to calculate a parameter R as follows:

$$R = \frac{RedAC/RedDC}{InfraRedAC/InfraRedDC},$$

wherein,

RedAC is an AC component of the light having the red wavelength;

RedDC is a DC component of the light having the red wavelength;

InfraRedAC is an AC component of the light having the infrared wavelength; and,

InfraRedDC is a DC component of the light having the infrared wavelength; and, wherein the device is adapted to measure SpO2 as a function of said parameter R.

6. A pulse oximetry device according to numbered paragraph 5, wherein the light detector is adapted to detect light reflected towards the device.

7. A pulse oximetry device according to numbered paragraph 5 or 6, wherein the reference pulse-oximeter is a medical-grade pulse-oximeter;
   optionally, wherein said reference pulse-oximeter is medically certified;
   optionally, wherein said reference pulse-oximeter comprises a clip probe and one or more wires for transmitting signals from the clip probe to a measurement unit of the reference pulse-oximeter;
   optionally, wherein said clip probe is a finger clip or an ear clip probe.

8. A device according to numbered paragraph 5, 6 or 7, wherein the one or more reference SpO2 values are measured using said reference pulse-oximeter on two or more test subjects;
   optionally, wherein the one or more reference SpO2 values are measured using said reference pulse-oximeter on a plurality of test subjects;
   optionally, wherein said plurality of test subjects is a large plurality of test subjects.

9. A device according to any one of numbered paragraphs 5-8, wherein the device comprises a memory and the calibration data are stored locally on said memory.

10. A device according to any one of numbered paragraphs 5-9, wherein the calibration data define a linear relationship between the SpO2 measurements and the parameter R.

11. A device according to any one of numbered paragraphs 5-10, wherein the device is adapted to perform at least one correction of the SpO2 measurements;
   optionally, wherein said correction depends on a target subject of the SpO2 measurements.

12. A device according to numbered paragraph 11, wherein said correction is based on at least one correction value;
   optionally, wherein said at least one correction value comprises an offset;
   optionally, wherein said offset is calculated as the difference between an SpO2 measurement performed by the device and a corresponding reference SpO2 value taken by the reference pulse-oximeter on a target subject of the SpO2 measurements.

13. A device according to any one of numbered paragraphs 1-12, wherein the device is in the form of pulse oximetry bracelet for measuring blood oxygenation on a wrist of a user, wherein said bracelet accommodates the one or more light emitters and the at least one light detector;
   optionally, wherein said bracelet includes said memory.

14. A device according to numbered paragraph 13, wherein said bracelet further comprises a processor programmed to perform said measurement of the one or more characteristics of the detected light and to perform said conversion.

15. A device according to any one of numbered paragraphs 1-14, further comprising visual and/or display means for producing an output related to the SpO2 measurements;
   optionally, wherein said means are adapted for monitoring the measured SpO2.

16. A system comprising, in combination, the device of any one of numbered paragraphs 1-15 and a docking station for docking the device thereto, wherein the device and the docking station are operable to exchange data therebetween;
   optionally, wherein the docking station is adapted to wirelessly recharge the device;
   optionally, wherein the docking station incorporates said reference pulse-oximeter.

17. A method of measuring blood oxygen levels using a pulse oximetry device, the method comprising:
   providing a pulse oximetry device for measuring blood oxygenation, the device comprising:
     one or more light emitters for emitting light directed into a human tissue,
     at least one light detector for detecting the light emitted from said one or more light emitters after the light has passed through said human tissue;
   measuring one or more characteristics of the detected light which can be converted into corresponding SpO2 measurements;
   converting said measured one or more characteristics into said SpO2 measurements based upon calibration data obtained from one or more reference SpO2 values measured using a different, reference pulse-oximeter.

18. A method of calibrating pulse oximetry blood oxygenation measurements, the method comprising:
   providing a first, reference pulse-oximeter adapted to measure reference SpO2 values on the basis of a predetermined pulse oximetry parameter;
   acquiring reference SpO2 values during multiple measurements carried out on each of one or more test subjects;
   from the reference SpO2 values, obtaining a calibration relationship that expresses SpO2 as a function of the predetermined pulse oximetry parameter;
   providing a second pulse oximetry device also adapted to measure the predetermined pulse oximetry parameter;
   using the second pulse oximetry device, performing one or more measurements of the predetermined pulse oximetry parameter on a target subject;
   converting said measurements into SpO2 measurements using said calibration relationship.

19. A method according to numbered paragraph 18, wherein the first, reference pulse-oximeter is a medical-grade pulse-oximeter;
   optionally, wherein said pulse-oximeter is medically certified.

20. A method according to numbered paragraph 19, wherein the first, reference pulse-oximeter comprises one or more wires for transmitting signals from at least one pulse oximetry probe to a central measurement unit;
  optionally, wherein said pulse oximetry probe is a finger or ear lobe probe.

21. A method according to numbered paragraph 18, 19 or 20, wherein the first, reference pulse-oximeter comprises at least one light emitters and at least one light detector adapted to detect light emitted by said light emitter after the light has passed through a human tissue;
  optionally, wherein the light detector is adapted to measure a light intensity.

22. A method according to numbered paragraphs 21, wherein the pulse-oximeter comprises two light emitters for emitting two respective substantially monochromatic lights at different wavelengths.

23. A method according to numbered paragraph 22, wherein said different wavelengths comprise a red wavelength and an infrared wavelength.

24. A method according to numbered paragraph 21, 22 and 23, wherein the predetermined pulse oximetry parameter is a parameter R calculated as follows:

$$R = \frac{RedAC/RedDC}{InfraRedAC/InfraRedDC},$$

wherein,
RedAC is an AC component of the light having the red wavelength;
RedDC is a DC component of the light having the red wavelength;
InfraRedAC is an AC component of the light having the infrared wavelength; and,
InfraRedDC is a DC component of the light having the infrared wavelength.

25. A method according to any one of numbered paragraphs 18-25, wherein obtaining said calibration relationship from said reference SpO2 values comprises interpolating said reference SpO2 values;
  optionally, wherein said interpolating comprises linearly interpolating said reference SpO2 values.

26. A method according to any one of numbered paragraphs 18-26, further comprising:
  storing the reference SpO2 values and/or said calibration relationship in a memory provided on the pulse oximetry device.

27. A method according to any one of numbered paragraphs 18-26, further comprising:
  correcting said reference SpO2 values and/or said calibration relationship;
  optionally, wherein said correcting depends on, or is specific to, the target subject;
  optionally, wherein said correcting comprises subtracting an offset value from said SpO2 values and/or from said calibration relationship.

28. A method according to any one of numbered paragraphs 18 to 27, wherein the second pulse oximetry device comprises a bracelet-type pulse oximetry device;
  optionally, wherein said pulse oximetry device comprises a case and a strap.

29. A method according to numbered paragraph 28, wherein the case accommodates a pulse oximetry unit comprising:
  two light emitters for emitting substantially monochromatic lights at different wavelengths comprising a red wavelength and an infrared wavelength; and,
  a light detector;
and wherein the strap comprises:
  a flexible elongated element connected to the case; and,
  wherein the method further comprises wearing the second pulse oximetry device to measure the SpO2 measurements around a wrist of the target subject.

30. A method according to any one of numbered paragraphs 18-29, wherein measuring the reference SpO2 values using the first, reference pulse-oximeter is carried out for each test subject over a first time period of less than one hour, or less than two hours, or less than five hours;
  optionally, wherein the first, reference pulse-oximeter is integrated into a docking station for docking the second pulse oximetry device.

31. A method according to any one of numbered paragraphs 18-30, wherein measuring the SpO2 measurements performed by the second pulse oximetry device are carried out over a second time period of at least five hours;
  optionally, at least 12 hours;
  optionally, at least 18 hours;
  optionally, at least 24 hours.

32. A method according to any one of numbered paragraphs 18-31, wherein the method further comprises:
  categorising the SpO2 measurements according to their values.

33. A method according to numbered paragraph 32, wherein the second pulse oximetry device comprises an accelerometer for measuring levels of activity relating to the target subject, and wherein the method further comprises:
  categorising the adjusted SpO2 measurement according to said levels of activity.

34. A wearable pulse oximetry device comprising:
  a housing defining a lower face for locating opposite a measurement target area of a target subject;
  at least one pulse oximetry module for performing pulse oximetry measurements;
  an elongated, flexible element connected to the housing for securing the housing on the target subject; wherein
  a projection extends from said lower face to define a contact surface between the housing and the measurement target area, and
  the pulse oximetry module cooperates with said projection to perform said pulse oximetry measurements.

35. A wearable pulse oximetry device according to numbered paragraph 34, wherein the pulse oximetry module comprises:
  two light emitters disposed within said housing, each light emitter for emitting a substantially monochromatic light, said lights having different wavelengths; and,
  at least one light detector for detecting emitted light reflected to the housing, said at least one detector being also disposed within the housing.

36. A wearable pulse oximetry device according to numbered paragraph 35, wherein both light emitters cooperate with said projection to inject their respective lights into the measurement target area.

37. A wearable pulse oximetry device according to numbered paragraph 35 or 36, wherein the light detector also cooperates with said projection to detect said reflected light.

38. A wearable pulse oximetry device according to any one of numbered paragraphs 34-37, wherein said projection defines a projection volume within said housing, and the pulse oximetry unit is located within said projection volume.

39. A wearable pulse oximetry device according to any one of numbered paragraph 34-38, wherein said projection is part-spherical;
optionally, wherein said projection is semi-spherical.

40. A wearable pulse oximetry device according to any one of numbered paragraphs 34-39, wherein said elongated, flexible element is in the form of a bracelet, and the housing is adapted to be worn around a wrist of the subject.

41. A wearable pulse oximetry device according to any one of numbered paragraphs 34-40, further comprising a printed circuit board for operating the device;
optionally, wherein said printed circuit board is located within said housing.

42. A wearable pulse oximetry device according to numbered paragraph 41, wherein said printed circuit board comprises, or is operatively connected to, any one or more of the following:
a memory;
a processor;
a data exchange module, optionally Bluetooth compatible;
a battery, optionally rechargeable;
a battery recharge module;
an accelerometer, optionally triaxial.

43. A wearable pulse oximetry device according to numbered paragraph 41 or 42, wherein the pulse oximetry module is provided as part of, or is operatively coupled to, said printed circuit board;
optionally, wherein the light emitters comprise one or more respective LED elements integrated into said circuit board;
optionally, wherein the light detector comprises a photodiode.

44. A wearable pulse oximetry device according to any one of numbered paragraphs 34-43, wherein the pulse oximetry device comprises a feedback feature for providing feedback to the target subject in relation to the SpO2 measurements;
optionally, wherein said feedback feature is visual;
optionally, wherein said visual feedback feature comprises an LED light;
optionally, wherein said LED light is disposed on an upper face of the housing;
optionally, wherein said LED light illuminates when at least one of the measured SpO2 values is below a predetermined level;
optionally, wherein said visual feedback feature comprises a display for displaying and/or monitoring one or more of the measured SpO2 values.

45. A wearable pulse oximetry device according to any one of numbered paragraphs 34-44, wherein the lower face comprises a friction surface for reducing or inhibiting displacement of the pulse oximetry device on the measurement target area.

46. A wearable pulse oximetry device according to numbered paragraph 45, wherein the friction surface surrounds said projection at least partially;
optionally, wherein the friction surface completely surrounds said projection;
optionally, wherein the friction surface is a side of a double sided adhesive tape applied to the lower face of the housing.

47. A pulse oximetry system comprising a wearable pulse oximetry device according to any one of numbered paragraphs 34 to 46.

48. The pulse oximetry system of numbered paragraph 47, wherein the system comprises a docking station for docking the wearable pulse oximetry device thereto;
optionally, wherein the docking station is adapted to recharge the rechargeable battery provided on the wearable pulse oximetry device;
optionally, wherein the pulse oximetry device is adapted to exchange data with the docking station;
optionally, wherein the docking station comprises a reference pulse-oximeter for calibrating the pulse oximetry device.

49. The pulse oximetry system of numbered paragraph 48, wherein the docking station is adapted to communicate with a personal computer and/or with a Cloud server for exchanging data therebetween.

50. A computer programme product comprising a computer readable medium comprising computer readable instructions stored thereon for performing a method according to any one of numbered paragraphs 17 or 18-33.

At least one embodiment of the present inventions has been described above in detail, purely to allow the skilled person to put the inventions into practice in many different ways.

Protection for the present invention is sought in accordance with the scope defined by the appended claims.

The invention claimed is:

1. A method of taking pulse oximetry measurements, the method comprising:
providing a first, reference pulse-oximeter adapted to measure reference Oxygen saturation (SpO2) values on a basis of a first predetermined pulse oximetry parameter calculated from a first, reference Photoplethysmography (PPG) signal measured by the reference pulse-oximeter on a non-wrist body portion sufficiently perfused with arterial blood of each of one or more test subjects;
using said first, reference pulse-oximeter, measuring reference SpO2 values for multiple measurements carried out on the non-wrist body portion of each of the one or more test subjects;
from the reference SpO2 values, obtaining a calibration relationship that expresses SpO2 as a function of the first predetermined pulse oximetry parameter;
providing a second, bracelet-type pulse oximetry device adapted to acquire SpO2 a second PPG signal on a wrist of a target subject, wherein the device is adapted to calculate therefrom a second predetermined pulse oximetry parameter;
using the second, bracelet-type pulse oximetry device, performing one or more acquisitions of the second PPG signal on the wrist of the target subject;
calculating from the one or more acquisitions of the second PPG signal one or more corresponding values of the second predetermined pulse oximetry parameter;
converting said one or more corresponding values of the second predetermined pulse oximetry parameter into measured SpO2 values using said calibration relationship.

2. The method according to claim 1, wherein the first predetermined pulse oximetry parameter and the second predetermined pulse oximetry parameter are the same parameter derived from respectively the first, reference PPG signal and the second PPG signal.

3. The method according to claim 1, wherein the first, reference pulse-oximeter is a medical-grade, medically certified pulse-oximeter.

4. The method according to claim 2, wherein the first, reference pulse-oximeter comprises at least one light emitter and at least one light detector adapted to detect light emitted by said light emitter after the light has passed through a human tissue;
wherein the light detector is adapted to measure a light intensity.

5. The method according to claim 4, wherein the first, reference pulse-oximeter comprises two light emitters for emitting two respective substantially monochromatic lights at different wavelengths, wherein said different wavelengths comprise a red wavelength and an infrared wavelength.

6. The method according to claim 5, wherein the first predetermined pulse oximetry parameter derived from the first, reference PPG signal and/or the second predetermined pulse oximetry parameter derived from the second PPG signal is a parameter R calculated as follows:

$$R = \frac{RedAC/RedDC}{InfraRedAC/InfraRedDC},$$

wherein,
RedAC is an amplitude of the alternating (AC) component of the light having the red wavelength;
RedDC is an amplitude of the continuous (DC) component of the light having the red wavelength;
InfraRedAC is an AC component of the light having the infrared wavelength; and,
InfraRedDC is a DC component of the light having the infrared wavelength.

7. The method according to claim 1, wherein obtaining said calibration relationship from said estimated reference SpO2 values comprises interpolating said estimated reference SpO2 values;
wherein said interpolating comprises linearly interpolating said estimated reference SpO2 values.

8. The method according to claim 1, further comprising:
storing the reference SpO2 values and/or said calibration relationship in a memory provided in the second, bracelet-type pulse oximetry device.

9. The method according to claim 1, further comprising:
correcting said reference SpO2 values and/or said calibration relationship;
wherein said correcting depends on, or is specific to, the target subject;
wherein said correcting comprises subtracting an offset value from said reference SpO2 values and/or from said calibration relationship.

* * * * *